US010098218B2

(12) United States Patent
Yamamoto et al.

(10) Patent No.: US 10,098,218 B2
(45) Date of Patent: Oct. 9, 2018

(54) TRANSPORTABLE LINEAR ACCELERATOR SYSTEM AND TRANSPORTABLE NEUTRON SOURCE EQUIPPED THEREWITH

(71) Applicant: MITSUBISHI ELECTRIC CORPORATION, Chiyoda-ku, Tokyo (JP)

(72) Inventors: Kazuo Yamamoto, Tokyo (JP); Sadahiro Kawasaki, Tokyo (JP); Hiromitsu Inoue, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 15/324,870

(22) PCT Filed: Sep. 3, 2014

(86) PCT No.: PCT/JP2014/073126
§ 371 (c)(1),
(2) Date: Jan. 9, 2017

(87) PCT Pub. No.: WO2016/035151
PCT Pub. Date: Mar. 10, 2016

(65) Prior Publication Data
US 2017/0223815 A1    Aug. 3, 2017

(51) Int. Cl.
*H05H 7/00* (2006.01)
*H05H 7/22* (2006.01)
(Continued)

(52) U.S. Cl.
CPC .......... *H05H 7/001* (2013.01); *G01N 23/025* (2013.01); *G21K 1/04* (2013.01); *H05H 7/02* (2013.01);
(Continued)

(58) Field of Classification Search
USPC ................... 250/251, 396 ML, 424
See application file for complete search history.

(56) References Cited

U.S. PATENT DOCUMENTS 2,816,243 A * 12/1957 Herb ......................... G21K 1/14
315/111.01
4,383,180 A * 5/1983 Turner ................. H01J 37/3171
250/398
(Continued)

FOREIGN PATENT DOCUMENTS

CN  103026802 A   4/2013
JP  05-258898 A   10/1993
(Continued)

OTHER PUBLICATIONS

International Search Report (PCT/ISA/210) dated Nov. 4, 2014, by the Japanese Patent Office as the International Searching Authority for International Application No. PCT/JP2014/073126.
(Continued)

*Primary Examiner* — Phillip A Johnston
(74) *Attorney, Agent, or Firm* — Buchanan Ingersoll & Rooney PC

(57) ABSTRACT

For the purpose of providing a transportable linear accelerator system which can restrain entering of losing ion beams deviated from a trajectory therefor, to thereby efficiently achieve reduction in radioactivity at low cost, and a transportable neutron source equipped therewith, a transportable linear accelerator system is configured to be provided with a beam chopper just before an inlet of a post-accelerator, thereby to cut off, from the proton beams pre-accelerated by a pre-accelerator, uncontrolled proton beams, and thus to radiate only the controlled proton beams to the post-accelerator, so that the proton beams are prevented from hitting an acceleration electrode, etc. of the post accelerator.

13 Claims, 9 Drawing Sheets

(51) Int. Cl.
 *G21K 1/04* (2006.01)
 *H05H 7/14* (2006.01)
 *H05H 7/02* (2006.01)
 *G01N 23/02* (2006.01)

(52) U.S. Cl.
 CPC ............... *H05H 7/14* (2013.01); *H05H 7/22* (2013.01); *H05H 2007/002* (2013.01)

(56) References Cited

U.S. PATENT DOCUMENTS

| | | | | |
|---|---|---|---|---|
| 4,578,589 | A * | 3/1986 | Aitken | H01J 37/3171 |
| | | | | 250/281 |
| 5,539,788 | A * | 7/1996 | Ruddy | G01N 23/222 |
| | | | | 250/253 |
| 6,320,334 | B1 * | 11/2001 | Roberge | H01J 37/304 |
| | | | | 250/492.2 |
| 8,836,247 | B2 * | 9/2014 | Yamamoto | H05H 9/042 |
| | | | | 315/500 |
| 9,442,213 | B2 * | 9/2016 | Bendahan | G01T 3/00 |
| 2010/0232559 | A1 | 9/2010 | Takeishi et al. | |
| 2013/0328506 | A1 | 12/2013 | Yamamoto et al. | |

FOREIGN PATENT DOCUMENTS

| | | |
|---|---|---|
| JP | 08-096995 A | 4/1996 |
| JP | 2003-257700 A | 9/2003 |
| JP | 2007-287538 A | 11/2007 |
| JP | 2009-187705 A | 8/2009 |
| JP | 2010-027529 A | 2/2010 |
| JP | 2014-017231 A | 1/2014 |
| JP | 2014-175279 A | 9/2014 |
| WO | WO 03/081604 A1 | 2/2003 |
| WO | WO 2007/142296 A1 | 12/2007 |

OTHER PUBLICATIONS

Written Opinion (PCT/ISA/237) dated Nov. 4, 2014, by the Japanese Patent Office as the International Searching Authority for International Application No. PCT/JP2014/073126.

Office Action (Notification of Reason for Refusal) dated Jun. 13, 2017, by the Japanese Patent Office in corresponding Japanese Patent Application No. 2016-546230, and an English Translation of the Office Action. (7 pages).

Office Action dated Jun. 28, 2018 in corresponding Chinese Patent Application No. 201480081684.0, and an English translation thereof.

* cited by examiner

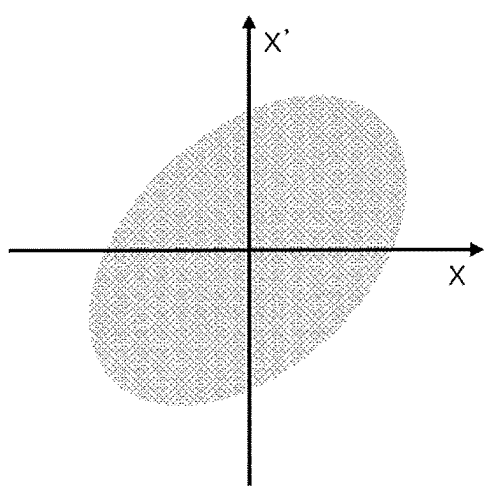
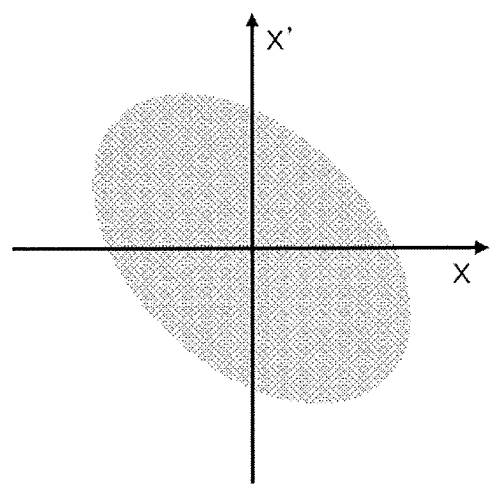
FIG. 4A                    FIG. 4B

TRANSPORTABLE LINEAR ACCELERATOR SYSTEM AND TRANSPORTABLE NEUTRON SOURCE EQUIPPED THEREWITH

TECHNICAL FIELD

The present invention relates to a transportable linear accelerator system for accelerating proton beams, and a transportable neutron source equipped therewith.

BACKGROUND ART

A transportable neutron source is an apparatus that radiates neutrons, while being placed or moved, after it is transported near a fixed object such as a bridge, to thereby perform non-destructive inspection thereof. The neutron source is configured with a linear accelerator system for generating proton beams and a target for generating neutron beams from the accelerated proton beams.

In the linear accelerator system, the proton beams are accelerated up to an energy of about 4 to 10 MeV that is required for efficiently generating the neutron beams. The linear accelerator system is configured with: an ion source for generating proton beams; a pre-accelerator for clustering and pre-accelerating the proton beams generated from the ion source; a post-accelerator for accelerating the beams up to the energy at which neutron beams are efficiently generated; and an amplifier for feeding beam accelerating power to the respective accelerators.

With respect to transportable linear accelerator systems, they are required to be transportable by use of an ordinary vehicle. In order to make the system transportable, such an on-board configuration of a linear accelerator system is disclosed in, for example, Patent Document 1, that is a compact apparatus but is capable of causing acceleration with a large current, and that comprises an ion source, a radio frequency quadrupole accelerator (Radio Frequency Quadrupole Linac; RFQ) and a drift tube accelerator (Drift Tube Linac; DTL).

However, in the conventional transportable linear accelerator systems, a copper material is used for the radio frequency quadrupole accelerator and the drift tube accelerator serving as the pre-accelerator and the post-accelerator, respectively, in order to enhance power efficiency. Thus, when the proton beams accelerated up to an energy of about 4 to 10 MeV hit an electrode in the above accelerators, neutrons are generated, so that a thick concrete is required to prevent the neutron from leaking out of the vehicle, making it difficult to reduce the total weight as a transportable system.

In this respect, such a technique is disclosed in, for example, Patent Document 2, that makes it possible to reduce radioactivity by applying gold or aluminum on an ion beam-facing inner surface or the like, of the quadrupole electromagnet or the drift tube electrodes in the accelerators.

CITATION LIST

Non Patent Document

Patent Document 1: International Publication No. WO2003-081604A1 (Page 4, Lines 14 to 21; FIG. 1)

Patent Document 2: Japanese Patent Application Laid-open No. 2007-287538 (Paragraph 0008; FIG. 5)

SUMMARY OF THE INVENTION

Problems to be Solved by the Invention

However, according to the configuration in Patent Document 2, there is a problem that, among the ion beams accelerated by the radio frequency quadrupole accelerator, uncontrolled losing ion beams are almost incident to the inside of the drift tube linear accelerator, and only the radioactivity of beams hitting the surface of the gold or aluminum applied on the beam-facing inner surface in each drift tube, can be reduced, so that it is not possible to reduce radioactivity sufficiently.

Further, there is a problem that, because gold or aluminum is applied on the beam-facing inner surface of each of several tens to several hundreds of drift tubes, this configuration is highly costly in view of material cost and manufacturing cost.

This invention has been made to solve the problems as described above, and an object thereof is to provide a transportable linear accelerator system which can restrain entering of uncontrolled losing ion beams, to thereby efficiently achieve reduction in radioactivity at low cost, and a transportable neutron source equipped therewith.

Means for Solving the Problems

A transportable linear accelerator system of the invention is characterized by comprising: a pre-accelerator that clusters and pre-accelerates proton beams generated by an ion source; a beam chopper that cuts off from the pre-accelerated proton beams, uncontrolled proton beams, to thereby cause only the proton beams controlled by the pre-accelerator to pass through the beam chopper; and a post-accelerator that accelerates up to a given energy the proton beams having passed through the beam chopper.

Effect of the Invention

According to the invention, the beam chopper is provided that cuts off from the proton beams pre-accelerated by the pre-accelerator, uncontrolled proton beams, so that only the proton beams controlled by the pre-accelerator are caused to pass through the beam chopper and radiated to the post-accelerator. Thus, it is possible to prevent the proton beams from hitting an acceleration electrode, etc. of the post accelerator, so that the generation of neutrons is suppressed. This allows the concrete for shielding against neutrons to be made thinner, thus making it possible to accommodate a more transportable type.

BRIEF DESCRIPTION OF THE DRAWINGS

FIG. 4A and FIG. 4B are diagrams illustrating a function of the beam chopper in the transportable linear accelerator system according to Embodiment 1 of the invention.

MODES FOR CARRYING OUT THE INVENTION

Embodiment 1

Figure 1:
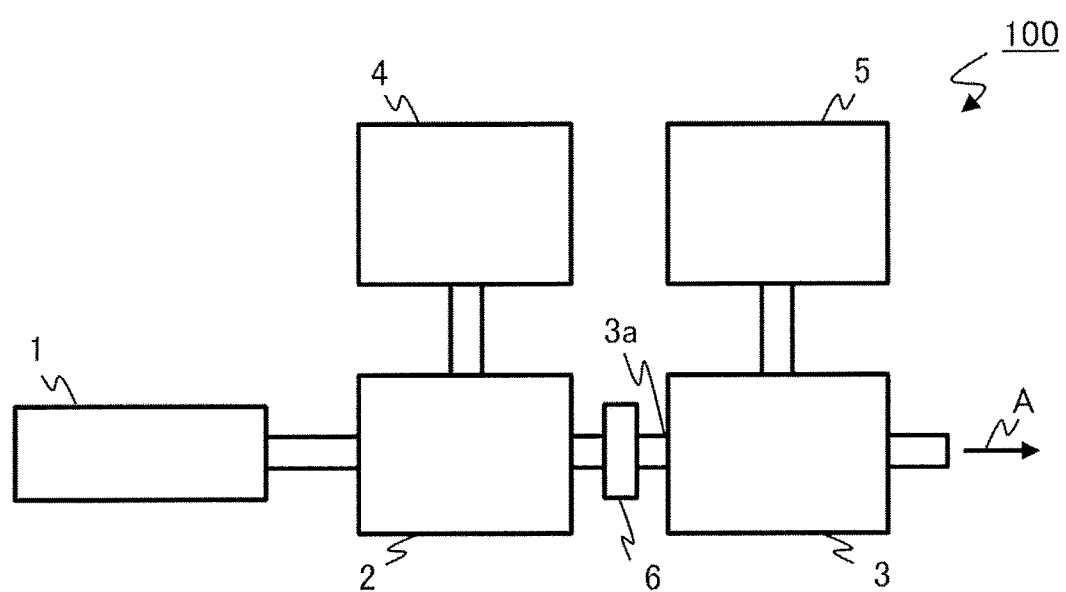
FIG. 1 is a configuration diagram showing a configuration of a transportable linear accelerator system according to Embodiment 1 of the invention.

FIG. 1 is a schematic diagram showing a configuration of a transportable linear accelerator system 100 according to Embodiment 1 of the invention. As shown in FIG. 1, the transportable linear accelerator system 100 is configured with: an ion source 1 that generates proton beams; a pre-accelerator 2 for clustering and pre-accelerating the proton beams generated from the ion source 1; a beam chopper 6 that allows only the proton beams accelerated and controlled by the pre-accelerator 2 to pass therethrough; a post-accelerator 3 that accelerates said beam up to an energy at which neutron beams are efficiently generated; and a high-frequency amplifier 4 and a high-frequency amplifier 5 that feed proton-beam accelerating power to the respective accelerators.

In the ion source 1, hydrogen is converted into plasma using an electric discharge to thereby generate proton beams, and the proton beams outputted from the ion source 1 are sent to the pre-accelerator 2.

Upon receiving power feeding from the high-frequency amplifier 4, the pre-accelerator 2 clusters and pre-accelerates the proton beams generated by the ion source 1, and then radiates them to the post-accelerator 3 through the beam chopper 6. Note that, at this stage, the energy of the proton beams is less than 4 MeV, so that if they hit a component part of the pre-accelerator 2, such as an acceleration electrode, an inner wall of its vacuum vessel, or the like, no neutron beam is generated.

The beam chopper 6 is provided just before an inlet 3a of the post-accelerator 3, and cuts off the proton beams non-clustered and uncontrolled by the pre-accelerator 2. This is because, if a part of the proton beams that is pre-accelerated but uncontrolled by the pre-accelerator 2 is incident to the post-accelerator 3 while remaining uncontrolled, and is then accelerated by the post-accelerator 3 up to an energy of about 4 to 10 MeV, the proton beams deviated from a trajectory therefor hit a component part of the post-accelerator 3, such as a copper-made acceleration electrode, an inner wall of its vacuum vessel, or the like, which results in the generation of neutron beams.

The post-accelerator 3 receives only the proton beams clustered and controlled by the pre-accelerator 2 and, upon receiving power feeding from the high-frequency amplifier 5, accelerates the proton beams pre-accelerated by the pre-accelerator 2, up to a required energy.

Figure 2:
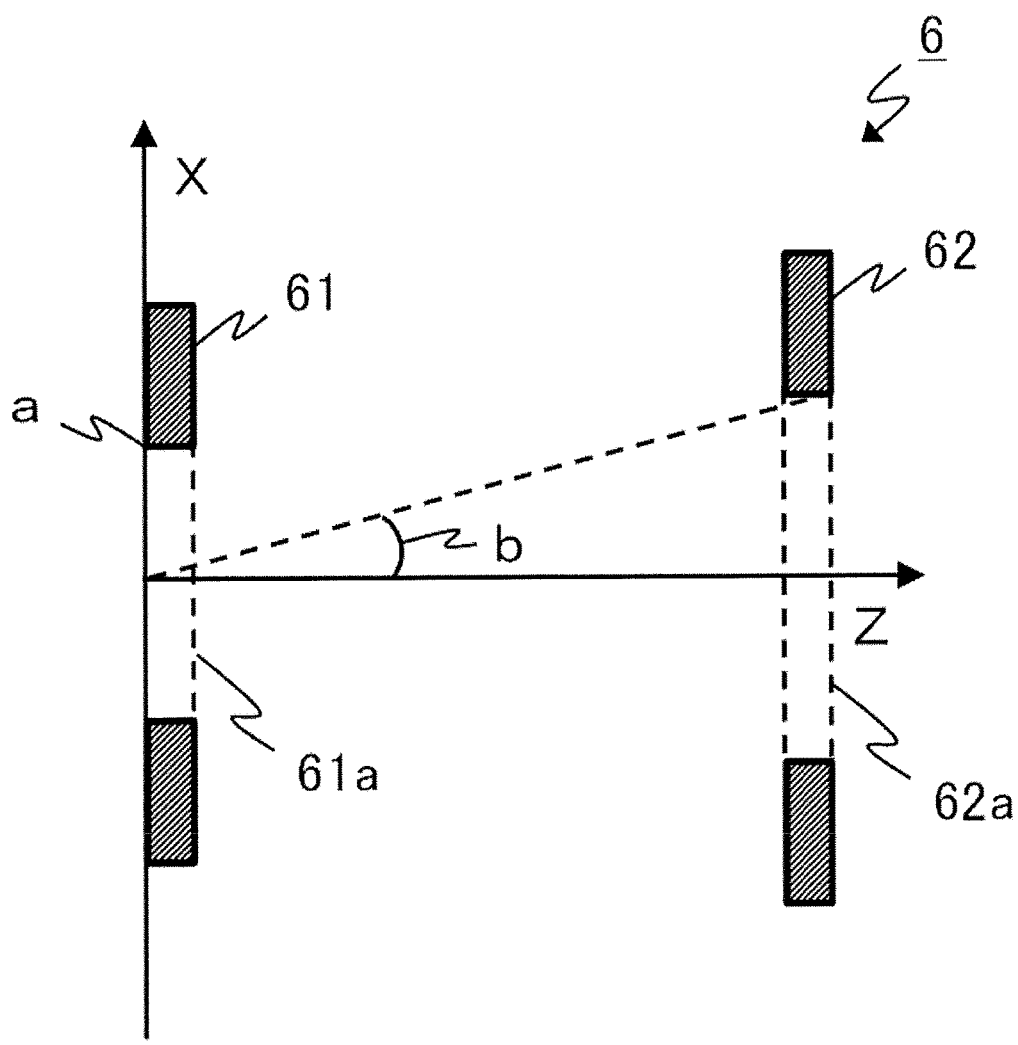
FIG. 2 is a diagram showing a configuration of abeam chopper in the transportable linear accelerator system according to Embodiment 1 of the invention.

FIG. 2 is a cross-sectional view showing a basic configuration of the beam chopper 6 in the transportable linear accelerator system 100 according to Embodiment 1 of the invention. As shown in FIG. 2, the beam chopper 6 is configured with two slits of a first slit 61 and a second slit 62 that are arranged perpendicular to a traveling direction Z of the proton beams. In the first slit 61 and the second slit 62, their respective circular-opening portions 61a, 61b are formed so that their opening lengths are adjustable.

Figure 3A:
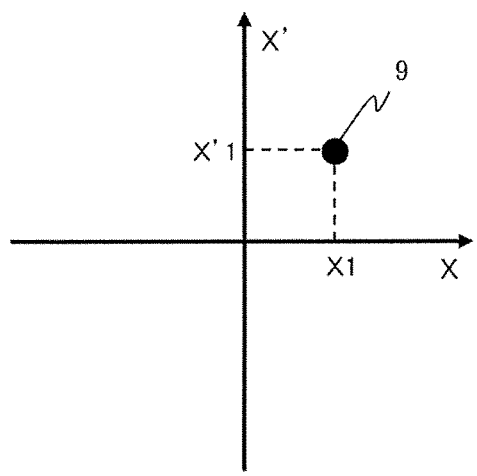
FIG. 3A and FIG. 3B are diagrams illustrating a function of the beam chopper in the transportable linear accelerator system according to Embodiment 1 of the invention.
Figure 3B:
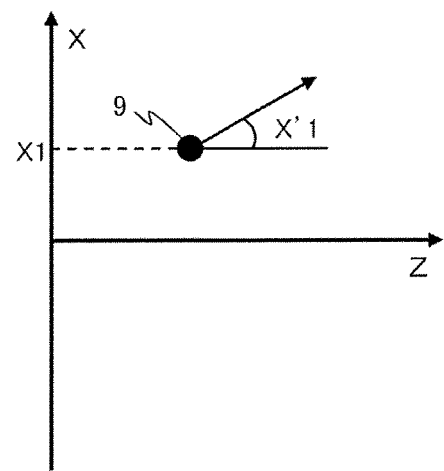

Here, description will be made using phase plane diagrams for indicating a beam characteristic of the proton beams to be subjected to filtering by the beam chopper 6, as a degree of breadth of the beams on a phase space. When a plane perpendicular to the traveling direction Z of the proton beams is defined separately by two axes of an X-axis and a Y-axis, FIG. 3A is a phase plane diagram for indicating a beam characteristic along the X-axis. In this phase plane diagram, the abscissa X represents a distance of one proton from the beam-acceleration center axis, and the ordinate X' means an angle of traveling direction of one proton 9 with respect to the beam-acceleration center axis. In FIG. 3A, it is shown that the one proton 9 is distant by X1 from the beam-acceleration center axis, and is directed at an angle of X'1 with respect to the beam-acceleration center axis. Modeling this into a motion with respect to the Z-axis, of the one proton 9 plotted in FIG. 3A, results in FIG. 3B.

FIG. 4A is a phase plane diagram in which illustrated are all positions and traveling-direction angles with respect to the Z-axis in a given beam traveling direction, of the respective protons in the proton beams. In FIG. 4A, the protons placed at positions apart from the beam-acceleration center axis also have angles directed away from the beam-acceleration center axis, which means that the beams are diverging beams. In contrast, FIG. 4B is a typical phase plane diagram of converging beams.

Figure 5:
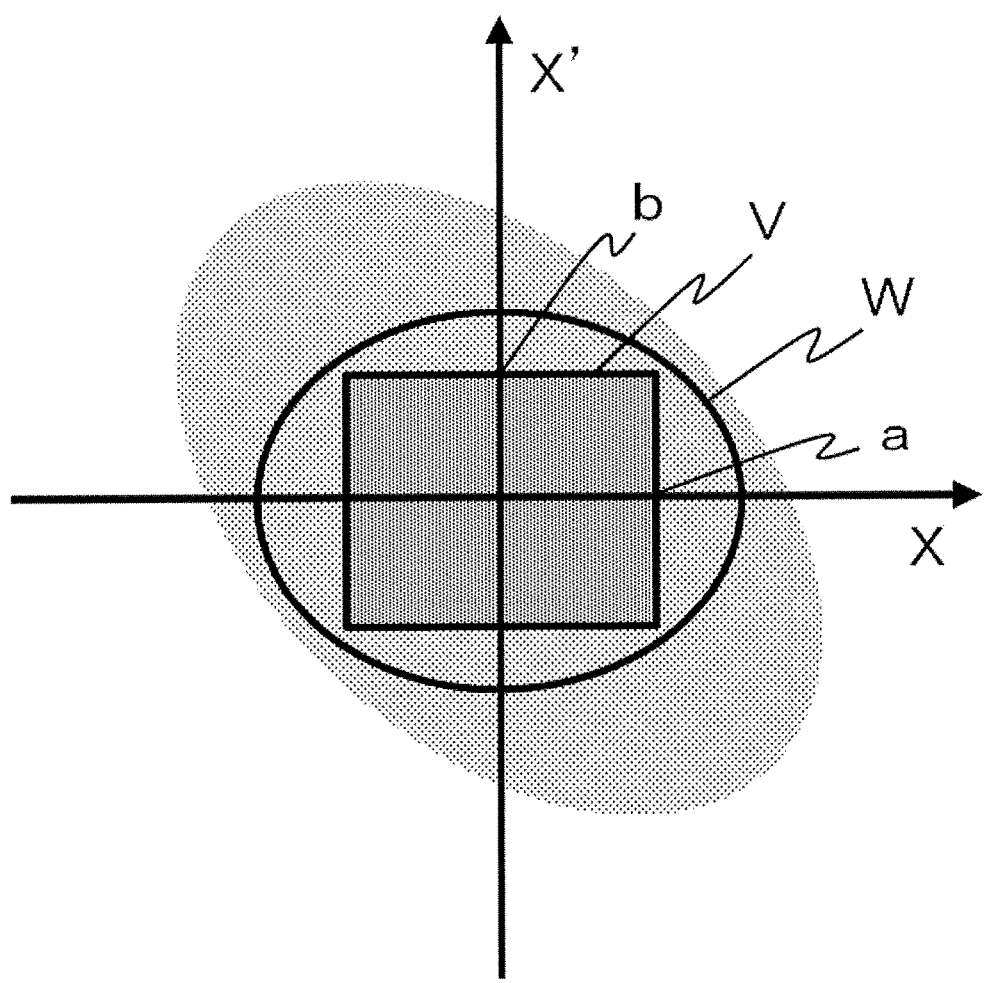
FIG. 5 is a diagram illustrating a function of the beam chopper in the transportable linear accelerator system according to Embodiment 1 of the invention.

FIG. 5 shows a region W of incident-beam distribution relative to the converging beams shown in FIG. 4B, in which the incident beams are allowed to pass through the accelerator.

Accordingly, in order to cause the proton beams being incident from the pre-accelerator 2 toward the post-accelerator 3 to pass therethrough, it is required to cause only the proton beams corresponding to the region W to be incident to the post-accelerator 3, by cutting off, from the proton beams coming from the ion source 1 and having passed through the pre-accelerator 2, proton beams other than the proton beams corresponding to the region W.

The beam chopper 6 is provided for cutting off the proton beams other than the proton beams corresponding to the region W. The beam chopper 6 is provided just before the inlet 3a of the post-accelerator 3, and in order to introduce the proton beams corresponding to the region W, as shown in FIG. 2, the opening length of the opening portion 61a in the first slit 61 is expanded up to a position a, and the opening portion 62a in the second slit 62 is expanded to have the opening length indicated by an angle b.

In this manner, adjusting the opening length of the first slit 61 and the opening length of the second slit 62 in the beam chopper 6, makes it possible to introduce only the proton beams corresponding to a region V (see, FIG. 5) that is included in the region W in which the proton beams being incident from the pre-accelerator 2 toward the post-accelerator 3 are allowed to pass therethrough, to thereby cut off proton beams other than the proton beams corresponding to the region W.

As a result, the proton beams pre-accelerated by the pre-accelerator 2 and being incident to the post-accelerator 3 are prevented from hitting the acceleration electrode, etc. of the post-accelerator 3, so that the generation of neutrons is suppressed and thus the concrete for shielding against neutrons can be made thinner. This makes it possible to accommodate a more transportable type, accordingly.

Note that, according to the conventional transportable linear accelerator system, the acceleration electrodes of the pre-accelerator and the post-accelerator are fixed by screw-fastening from the inner side in their vacuum vessels, and the screws for fixing the acceleration electrodes to the vacuum vessels will be loosened by vibration due to the transportability. Thus, there is also a problem that the screws in the vacuum vessel have to be re-fastened after releasing vacuum at every maintenance work, or the vacuum vessel has to be once disassembled because of the structure without expectation of screw loosening.

For dealing therewith, it is preferable to apply the configuration of a drift tube linear accelerator disclosed in Japanese Patent Application Laid-open No. 2014-17231 to the pre-accelerator 2 and the post accelerator 3.

Figure 6:
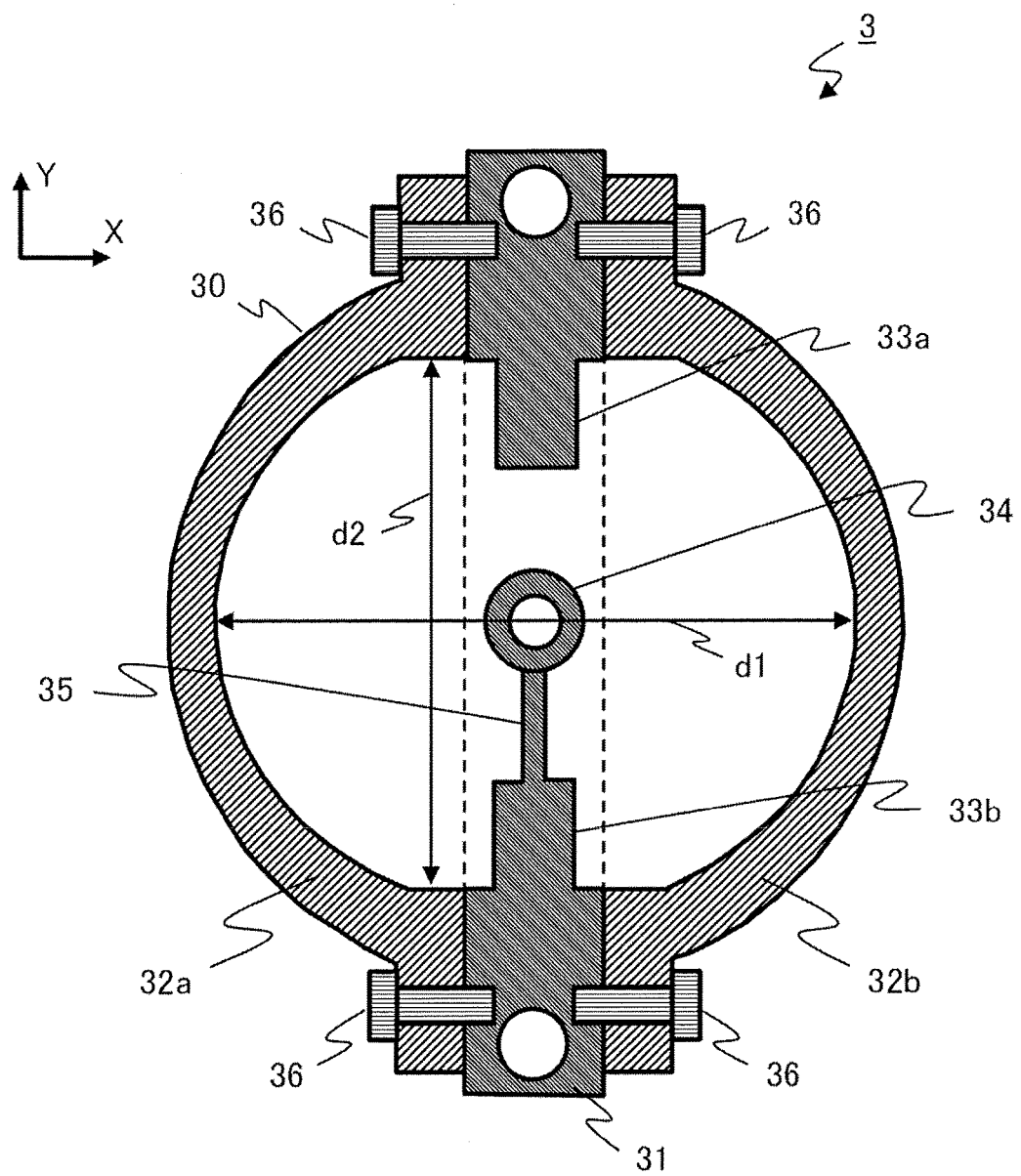
FIG. 6 is a diagram showing a post-accelerator in the transportable linear accelerator system according to Embodiment 1 of the invention.

FIG. 6 is a cross-sectional view showing a basic configuration of the post-accelerator 3 in the transportable linear accelerator system 100 according to Embodiment 1 of the invention, in which the configuration of the abovementioned drift tube linear accelerator is applied. As shown in FIG. 6, the vacuum vessel 30 of the post-accelerator 3 is formed of a central plate 31 and a pair of semi-cylindrical tubes 32a, 32b, and the central plate 31 has a ridge 33, an acceleration electrode 34 and a stem 35 connecting the ridge 33 with the acceleration electrode 34, that are made from a common block. Because of this configuration, the acceleration electrode 34 is fixed by screws 36 from the atmospheric side of the vacuum vessel 30, so that it is possible from the atmospheric side, to re-fasten the screws loosened by vibration at the time of transportation.

It is also preferable that the vacuum vessel 30 have, in its cross-section perpendicular to the beam-acceleration center axis, an X-direction inner diameter d1 of the vacuum vessel 30 that is perpendicular to a center axis in a planar direction of the central plate 31 which is a direction in which the stem 35 extends, and that passes across the beam-acceleration center axis, wherein the X-direction inner diameter is made longer than Y-direction inner diameter d2 of the vacuum vessel 30 that is parallel to the center axis in the planar direction. Because of this configuration, it is possible to adjust the electric-field distribution without using an external tuner, to thereby achieve power reduction.

Accordingly, applying the configuration of the drift tube linear accelerator disclosed in Japanese Patent Application Laid-open No. 2014-17231, to the transportable linear accelerator system 100 according to Embodiment 1 of the invention, makes it possible to accommodate a more transportable type.

Figure 7:
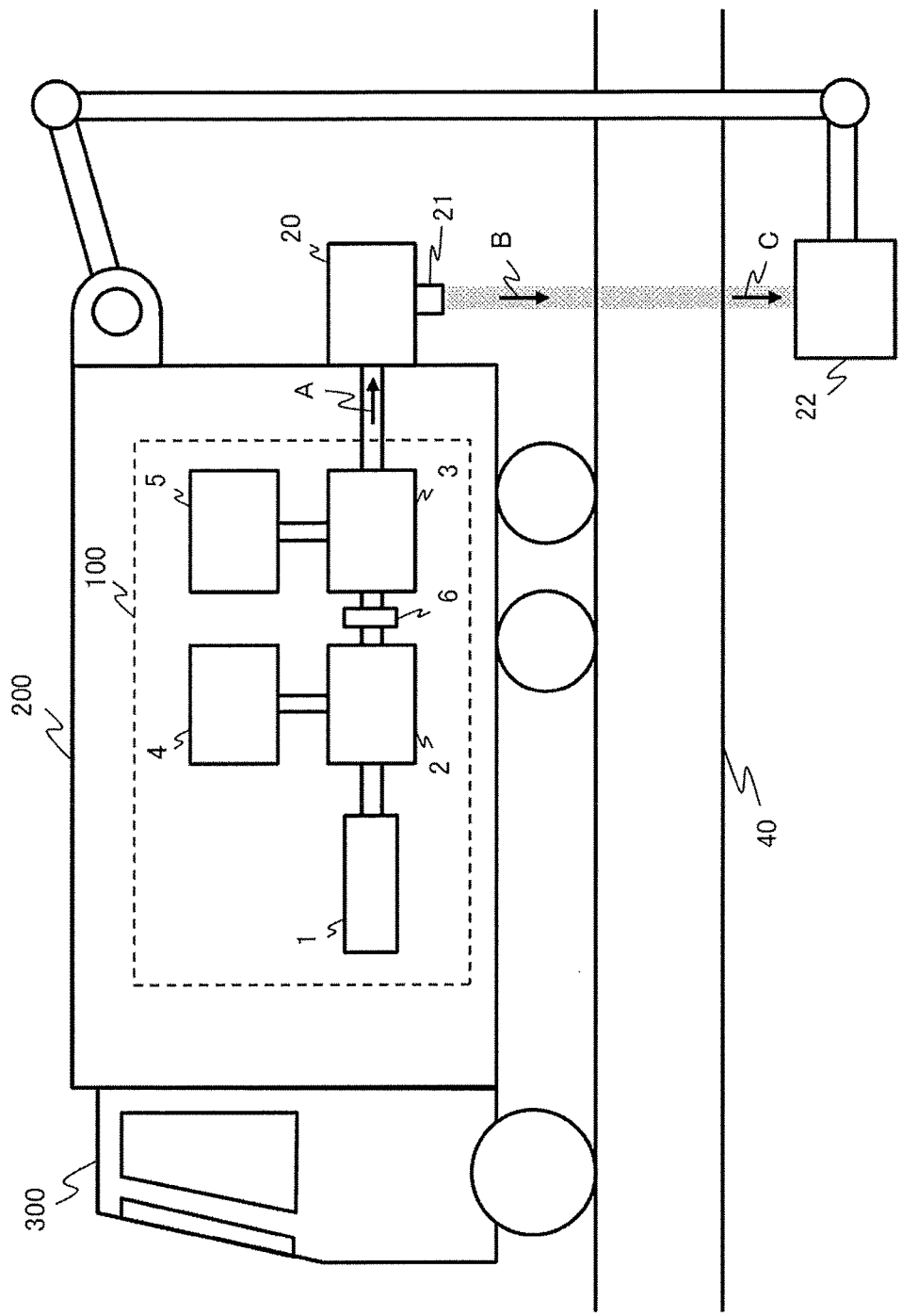
FIG. 7 is a diagram showing a usage example of a transportable neutron source including the transportable linear accelerator system according to Embodiment 1 of the invention.

Next, operations of the transportable linear accelerator system 100 according to Embodiment 1 of the invention will be described. FIG. 7 is a schematic diagram of a transportable neutron source 200 including the transportable linear accelerator system 100 according to Embodiment 1 of the invention. As shown in FIG. 7, the transportable neutron source 200 is configured with: the transportable linear accelerator system 100 that generates the proton beams; a target part 20 that generates neutron beams from the accelerated proton beams; and a neutron detector 22 that detects neutrons after being radiated from the target part 20 and passing through an intended object 40 to be measured.

First of all, in the transportable linear accelerator system 100, proton beams are generated at the ion source 1, and the proton beams outputted from the ion source 1 are incident to the pre-accelerator 2.

Subsequently, the proton beams being incident from the ion source 1 to the pre-accelerator 2, are clustered and pre-accelerated by the pre-accelerator 2, and are then incident, after passing through the beam chopper 6, to the post-accelerator 3. The proton beams that passed through the beam chopper 6 are only the controlled proton beams resulted from cutting off proton beams non-clustered and uncontrolled by the pre-accelerator 2.

Then, the controlled proton beams are incident to the post-accelerator 3, and are then accelerated by the post-accelerator 3 from the pre-accelerated state up to an energy of about 4 to 10 MeV.

In this manner, in the transportable linear accelerator system 100, because the beam chopper 6 is used, the uncontrolled proton beams is cut off from the proton beams pre-accelerated by the pre-accelerator 2, so that only the controlled proton beams are incident to the post-accelerator 3. Thus, it is possible to prevent the proton beams from hitting the acceleration electrode, etc. of the post-accelerator, so that the generation of neutrons is suppressed and thus the concrete for shielding against neutrons can be made thinner. This makes it possible to accommodate a more transportable type.

As shown in FIG. 7, proton beams A accelerated in the transportable linear accelerator system 100 up to the energy at which neutron beams are efficiently generated, are introduced from the post-accelerator 3 into the target part 20 that is provided with a shield and a moderator. In the target part 20, the introduced proton beams A are radiated to target cells (not shown) in the target part 20, so that neutrons are generated. The generated neutrons are moderated by the moderator to a speed matched to the intention and are thereafter, radiated from a radiation port 21 as neutron beams B for non-destructive inspection. Note that, in order to irradiate the intended object 40 to be inspected (here, it is assumed to be a bridge, for example), the radiation port 21 is formed so that its radiation direction is adjustable.

After the transportable neutron source 200 is transported near the object 40 by a vehicle 300, the neutron beams B for non-destructive inspection are radiated to the object 40 while the neutron source is being placed, or moved above the object 40. The neutron beams B passes through the object 40, so that transmitted neutron beams C are radiated from the object 40.

The transmitted neutron beams C transmitted through the object 40 are captured by the neutron detector 22. Note that the neutron detector 22 is movably placed at a position where the transmitted neutron beams C can be captured.

In this manner, by the use of the transportable neutron source 200 including the transportable linear accelerator system 100, it is possible to non-destructively inspect the inside of a large structure, such as a bridge or the like, at its site.

As described above, in the transportable linear accelerator system 100 according to Embodiment 1 of the invention, the beam chopper 6 is provided just before the inlet 3a of the post-accelerator 3, thereby to cut off, from the proton beams pre-accelerated by the pre-accelerator 2, uncontrolled proton beams, and thus to make only the controlled proton beams incident to the post-accelerator 3. Thus, it is possible to prevent the proton beams from hitting the acceleration electrode, etc. of the post-accelerator, so that the generation of neutrons is suppressed and thus the concrete for shielding against neutrons can be made thinner. This makes it possible to accommodate a more transportable type.

Further, a configuration of the drift tube linear accelerator is applied, so that the vacuum vessel 30 of the post-accelerator 3 is formed of the central plate 31 and the pair of semi-cylindrical tubes 32a, 32b, and the central plate 31 has the ridge 33, the acceleration electrode 34 and the stem 35 connecting the ridge 33 with the acceleration electrode 34, that are made from a common block. Thus, the acceleration electrode is fixed using screws from the atmospheric side of the vacuum vessel, so that it is possible from the atmospheric side, to re-fasten the screws loosened by vibration at the time of transportation. Furthermore, the vacuum vessel 30 has, in its cross-section perpendicular to the beam-acceleration center axis, the X-direction inner diameter d1 of the vacuum vessel 30 that is perpendicular to a center axis in the planar direction of the central plate 31 which is a direction in which the stem 35 extends, and that passes across the beam-acceleration center axis, wherein the X-direction inner diameter is made longer than the Y-direction inner diameter d2 of the vacuum vessel 30 that is parallel to the center axis in the planar direction. Thus, it is possible to adjust the electric-field distribution without using an external tuner, to thereby achieve power reduction. This makes it possible to accommodate a more transportable type, accordingly.

Further, because the transportable linear accelerator system 100 is included in the transportable neutron source 200, it is possible for the source to accommodate a transportable type, so that the inside of a large structure, such as a bridge or the like, can be non-destructively inspected at its site.

Figure 8:
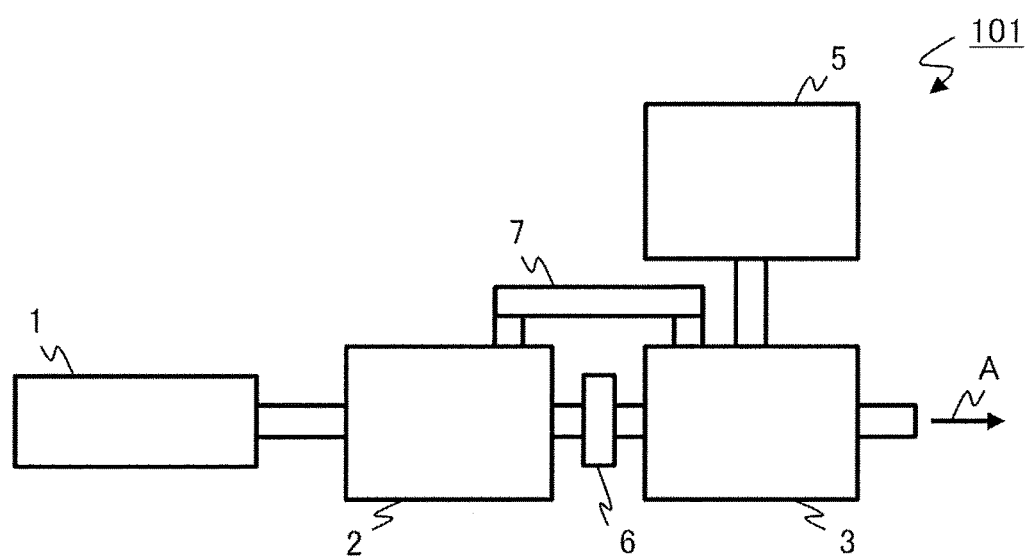
FIG. 8 is a configuration diagram showing a configuration of another transportable linear accelerator system according to Embodiment 1 of the invention.

Note that, in Embodiment 1, the pre-accelerator 2 and the post-accelerator 3 are provided, respectively, with the high-frequency amplifier 4 and the high-frequency amplifier 5 for feeding beam accelerating power; however, this is not limitative. As shown in a transportable linear accelerator system 101 shown in FIG. 8, it is allowable that the pre-accelerator 2 and the post-accelerator 3 are also connected electrically to each other by way of a power divider 7, and the power is fed from a single high-frequency amplifier 5 to the two accelerators as the pre-accelerator 2 and the post-accelerator 3. When the high-frequency amplifier 4 and the high-frequency amplifier 5 are vacuum-tube amplifiers that are sensitive to vibrations, reducing the number of the vacuum-tube amplifiers from two to one according to the above configuration also makes it possible to accommodate a transportable type. Note that, in FIG. 8, the post-accelerator 3 is provided with the high-frequency amplifier 5; however, a similar effect will, of course, be achieved when, instead, the pre-accelerator 2 is configured to be provided with a single high-frequency amplifier 4.

Figure 9:
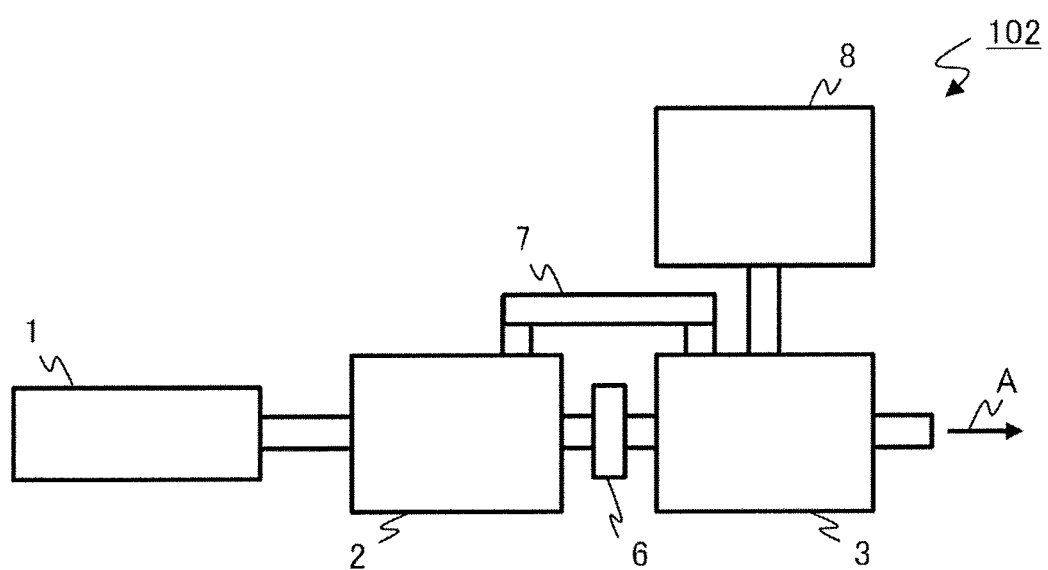
FIG. 9 is a configuration diagram showing a configuration of another transportable linear accelerator system according to Embodiment 1 of the invention.

Furthermore, as shown in a transportable linear accelerator system 102 shown in FIG. 9, it is allowable to configure so that, in place of the high-frequency amplifier 5 as the vacuum tube amplifier in the transportable linear accelerator system 101, an amplifier 8 configured with a semiconductor element is provided. Because no vacuum tube amplifier sensitive to vibrations is used, this configuration makes it possible to accommodate a more transportable type.

It should be noted that appropriate modification and omission in the embodiment may be made in the present invention without departing from the scope of the invention.

DESCRIPTION OF REFERENCE NUMERALS AND SIGNS

1: ion source, 2: pre-accelerator, 3: post-accelerator, 4: high-frequency amplifier, 5: high-frequency amplifier, 6: beam chopper, 7: power divider, 8: high-frequency amplifier, 20: target part, 22: neutron detector, 30: vacuum vessel, 31: central plate, 32a, 32b: semi-cylindrical tube, 33: ridge, 34: acceleration electrode, 35: stem, 61: first slit, 62: second slit, 100: transportable linear accelerator system, 101: transportable linear accelerator system, 102: transportable linear accelerator system, 200: transportable neutron source.

The invention claimed is:

1. A transportable neutron source, comprising:
a linear accelerator system, the linear accelerator system comprising:
a pre-accelerator that clusters and pre-accelerates proton beams generated by an ion source,
a beam chopper that cuts off, from the pre-accelerated proton beams, proton beams deviated from a trajectory therefor, to thereby cause only the proton beams controlled by the pre-accelerator to pass through the beam chopper, and
a post-accelerator that accelerates up to a given energy the proton beams having passed through the beam chopper;
a target part that introduces the proton beams from the transportable linear accelerator system to thereby generate neutron beams; and
a detector that captures the neutron beams after being radiated from the target part to an object and passing through the object.

2. The transportable neutron source according to claim 1, wherein, when a plane perpendicular to a traveling direction Z of the pre-accelerated proton beams is defined separately by two axes of an X-axis and a Y-axis, the beam chopper comprises: a first slit that causes, among the pre-accelerated proton beams, only the proton beams existing within a specified distance along the X-axis from a beam-acceleration center axis, to pass therethrough; and a second slit that causes, among the proton beams having passed through the first slit, only the proton beam existing within a specified angle from the first slit with respect to the beam-acceleration center axis, to pass therethrough.

3. The transportable neutron source according to claim 2, wherein the pre-accelerator and the post-accelerator are each a drift tube linear accelerator; a vacuum vessel of each of the pre-accelerator and the post-accelerator is formed of a central plate and a pair of semi-cylindrical tubes; and the central plate has a ridge, an acceleration electrode and a stem connecting the ridge with the acceleration electrode, that are made from a common block.

4. The transportable neutron source according to claim 3, wherein the vacuum vessel has, in its cross-section perpendicular to the beam-acceleration center axis, an X-direction vessel inner diameter that is perpendicular to a center axis in a planar direction of the central plate which is a direction in which the stem extends, and that passes across the beam-acceleration center axis,
said X-direction vessel inner diameter being longer than a Y-direction vessel inner diameter that is parallel to the center axis in the planar direction.

5. The transportable neutron source according to claim 1, wherein the pre-accelerator and the post-accelerator are connected to each other by way of a power divider, and the pre-accelerator or the post-accelerator is provided with a high-frequency amplifier that feeds power for accelerating the proton beams.

6. The transportable neutron source according to claim 2, wherein the pre-accelerator and the post-accelerator are connected to each other by way of a power divider, and the pre-accelerator or the post-accelerator is provided with a high-frequency amplifier that feeds power for accelerating the proton beams.

7. The transportable neutron source according to claim 3, wherein the pre-accelerator and the post-accelerator are connected to each other by way of a power divider, and the pre-accelerator or the post-accelerator is provided with a high-frequency amplifier that feeds power for accelerating the proton beams.

8. The transportable neutron source according to claim 4, wherein the pre-accelerator and the post-accelerator are connected to each other by way of a power divider, and the pre-accelerator or the post-accelerator is provided with a high-frequency amplifier that feeds power for accelerating the proton beams.

9. The transportable neutron source according to claim 5 wherein the high-frequency amplifier is configured with a semiconductor element.

10. The transportable neutron source according to claim 6, wherein the high-frequency amplifier is configured with a semiconductor element.

11. The transportable neutron source according to claim 7, wherein the high-frequency amplifier is configured with a semiconductor element.

12. The transportable neutron source according to claim 8, wherein the high-frequency amplifier is configured with a semiconductor element.

13. A linear accelerator system, comprising:
a pre-accelerator that clusters and pre-accelerates proton beams generated by an ion source, the pre-accelerator being a drift tube linear accelerator having a vacuum vessel comprising a central plate and a pair of semi-cylindrical tubes;
a beam chopper that cuts off, from the pre-accelerated proton beams, proton beams deviated from a trajectory therefor, to thereby cause only the proton beams controlled by the pre-accelerator to pass through the beam chopper; and
a post-accelerator that accelerates up to a given energy the proton beams having passed through the beam chopper, the post accelerator being a drift tube linear accelerator having a vacuum vessel comprising a central plate and a pair of semi-cylindrical tubes;
wherein, for each of the pre-accelerator and the post-accelerator: (i) the central plate has a ridge, an acceleration electrode and a stem connecting the ridge with the acceleration electrode, that are made from a common block, (ii) the semi-cylindrical tubes are provided on both sides of the center plate in a cross-sectional view, and (iii) the acceleration electrode of the central plate is fixed by screws from the atmospheric side of the vacuum vessel.

* * * * *